United States Patent [19]

Fuderer

[11] Patent Number: 5,608,083
[45] Date of Patent: Mar. 4, 1997

[54] PROCESS FOR THE PRODUCTION OF PHTHALIC ANHYDRIDE

[76] Inventor: Andrija Fuderer, Wielewaalstrasse 22, 2610 Antwerpen, Belgium

[21] Appl. No.: 417,798

[22] Filed: Apr. 6, 1995

[30]       Foreign Application Priority Data

Apr. 13, 1994  [DE]  Germany .......................... 44 12 737.5

[51] Int. Cl.⁶ ................................................. C07D 307/89
[52] U.S. Cl. .......................... 549/249; 549/240; 549/247; 549/248
[58] Field of Search .................................... 549/240, 247, 549/248, 249

[56]            References Cited

U.S. PATENT DOCUMENTS

| | | | |
|---|---|---|---|
| 3,892,781 | 7/1975 | Montgomery et al. | 260/346.4 |
| 4,435,581 | 3/1984 | Miserlis | 549/248 |
| 4,675,420 | 6/1987 | Block et al. | 549/248 |
| 5,225,574 | 7/1993 | Aichenger et al. | 549/248 |
| 5,245,093 | 9/1993 | Ember | 549/266 |

*Primary Examiner*—Joseph McKane
*Assistant Examiner*—Richard S. Myers, Jr.
*Attorney, Agent, or Firm*—Michael J. Striker

[57]                ABSTRACT

The process for making phthalic anhydride by catalytic gas phase oxidation of o-xylene or naphthalene includes feeding a gas containing oxygen and the reactant to a first reactor; operating the first reactor to oxidize the reactant and obtain an effluent gas including the reactant, phthalic anhydride and/or maleic anhydride; adding the reactant or a gas containing the reactant to the effluent so that a molar ratio of moles of free oxygen to a sum of moles of the organic compounds in the effluent is less than 7, preferably from 3 to 6; after that, feeding the effluent into a second reactor; and operating the fixed bed reactor to at least partially convert the reactant in the effluent to phthalic anhydride. In preferred embodiments the gas fed to the first reactor is controlled so that it is in the range of the lower inflammability limit and, after separating phthalic anhydride from the effluent, from 15 to 35% of the resulting waste gas is blended with fresh air, compressed to form a gas mixture and then recycled.

18 Claims, 1 Drawing Sheet

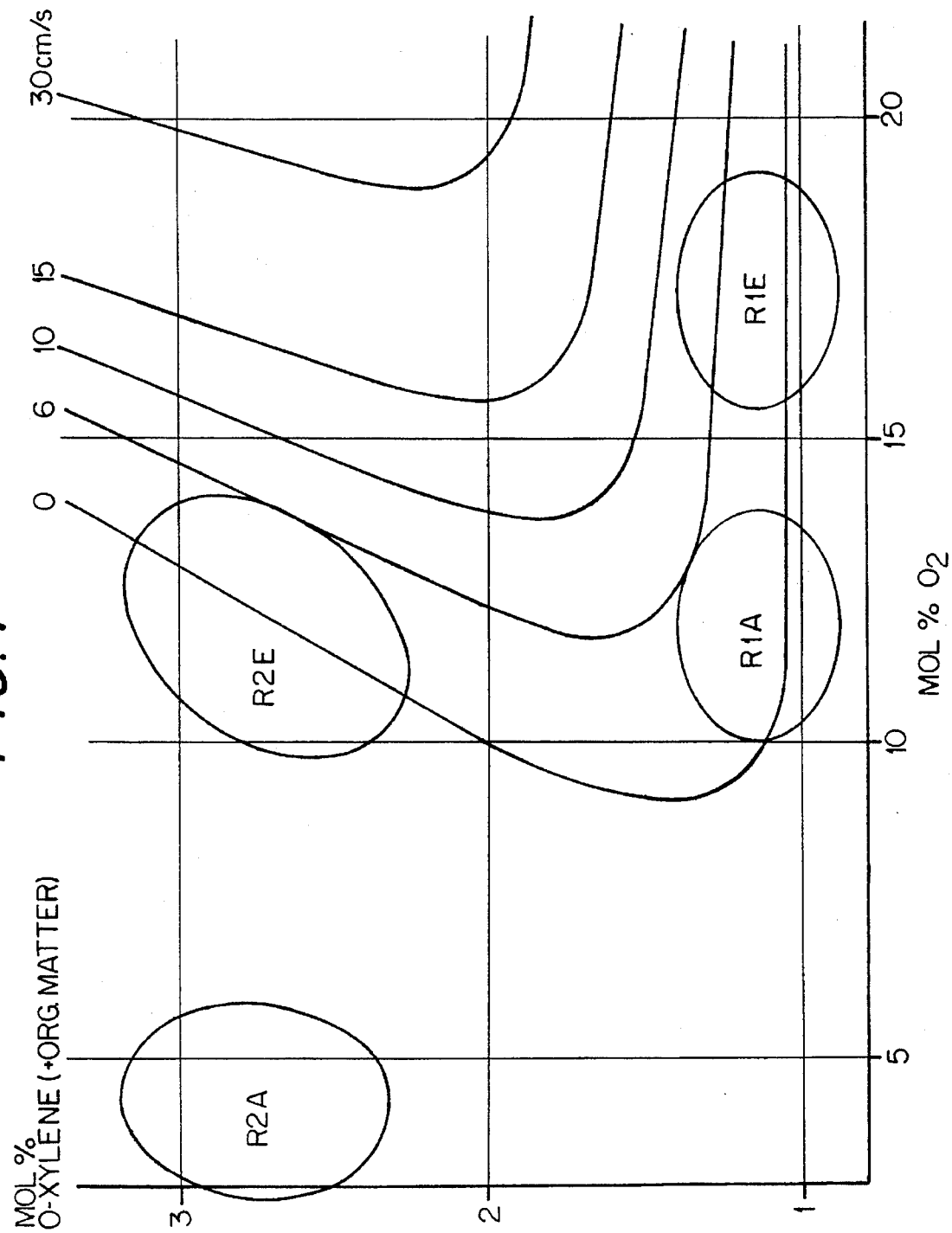

PROCESS FOR THE PRODUCTION OF PHTHALIC ANHYDRIDE

BACKGROUND OF THE INVENTION

The invention comprises a process for making phthalic anhydride and, more particularly, by oxidation of either naphthalene or o-xylene.

Phthalic arthydride is produced by catalytic oxidation of naphthalene or preferably o-xylene. Air or a gas obtained by mixing air with recycled off gas is used as oxidizing gas. The lower limit of inflammability is about 1 mol % o-xylene. Earlier processes were operated below the lower inflammability limit. Later, in order to reduce the flow of air and gas, the process was operated in the inflammable range and in recent processes the gas at the reactor inlet contains up to 1.4 mol % or about 70 grams per standard cubic meters of gas. The disadvantage of these processes is the high gas flow, which leads to high compression power, large diameter of the reactor and high costs of separation of the phthalic anydride from the Reaction gas. In another process, more than 50% of the off gas is recycled, mixed with fresh air, whereby a gas containing only 10–11% oxygen is obtained, which is outside of the inflammable range at any content of o-xylene. Therefore this process can be safely operated at 1.8 mol % o-xylene. However even in this latter process the gas flow and the compression power remain almost equally high.

Tubular reactors are used in most cases. The cooling of the reactor is achieved with a molten salt bath. The molten salt flows in the shell side of the reactor generally countercurrent to the direction of gas which flows inside the tubes containing the catalyst. The hot molten salt from the reactor is cooled in an exchanger in which high pressure steam is produced. The molten salt is then recycled to the reactor. The number of the tubes and the reactor diameter are determined by the gas flow and the allowable pressure drop. For example if at a given gas flow the reactor diameter is reduced by only 20% the gas pressure drop doubles. The length of the tubes is then determined by the required mass of catalyst and the quantity of heat to be removed. If the temperature of the salt bath is low, the reaction rate is also low and the conversion unsatisfactory. At too high salt temperature, the peak and the outlet temperature become excessive and the product yield is low. Therefore at a given catalyst mass and tube length the salt bath temperature must be controlled in a narrow range to obtain both satisfactory yield and conversion. The best temperature of the salt melt depends also on the direction of flow. In the first part of the reactor, more heat is produced than removed and the temperature of the gas rapidly rises to its peak level between 440° and 500° C. The largest portion of the feed is converted in the first part of the reactor. In the second part of the reactor the reaction is being completed, the heat removal is predominant and the gas temperature is dropping. A disadvantage of the existing processes is that due to the high gas flow the reactor diameter becomes very large and the transport of the reactor becomes very difficult. In case of large reactors with diameters between 5 and 6 meters the tube sheets are very expensive.

SUMMARY OF THE INVENTION

The objective of the process according to the invention is to dramatically reduce the flow of gas in all the apparatus components. At the greatly reduced flow the cost of most of the apparatus components is substantially lower and the energy required to compress and heat the gas and to recover the product is much lower. Also, the flow of the waste gas eventually vented to the atmosphere is significantly reduced. It was found that these objectives can be reached by arranging two reactors in series, adding feedstock to the effluent gas of the first reactor and introducing the thus obtained gas to a second reactor.

Typically between 55 and 70% of the phthalic arthydride is produced in the second reactor. Preferably, between 15 and 35% of the waste gas is recycled and mixed with fresh air, and the gas being compressed contains preferably between 15 and 18% oxygen. The compressed gas is preheated and after the addition of between 1 and 1.4 mol % feedstock it is introduced into the first reactor. The operating conditions in this first reactor are similar to those used in known processes, but the gas flow through the reactor is two or even three times lower and the reactor diameter 25–35% smaller, for example only 4.5 m instead of 6 m. It is important and advantageous, that in the first reactor, a complete conversion is not required and therefore compared with a conventional reactor, the length of the tubes can be reduced by about 30% as well. Therefore, the exit temperature is higher than in the conventional process and it is important to circulate the molten salt countercurrent to the gas. The inlet temperature and the mass flow of the molten salt can also be then lower than conventional.

Since a conversion of 90–98% is satisfactory, it is possible to use a fluid bed for the first reactor. The cooling of the fluid bed reactors is done either by circulated molten salt and/or by water evaporating at high pressure. The gas preheating in case of a fluid bed reactor is not needed. The reaction gas of the first reactor contains typically between 0.8 and 1.1 mol % phthalic arthydride and 11–14% oxygen. This reaction gas is preferably cooled below 380° C. in a heat exchanger or by the addition of cold gas. By further addition of liquid feedstock the temperature drops by some 50° C. lower.

For the safety of the process, the composition of the gas at the inlet and outlet of both reactors is important. The limits of inflammability as a function of oxygen and o-xylene molar percents is indicated in the appended figure. The lower inflammability limit is at around 1.1 mol % of o-xylene at any oxygen content above 10%, while the upper limit rises with increasing oxygen content and is at about 3 mol % o-xylene at an oxygen content of 13 mol %. Mixtures in which the molar ratio of free oxygen to o-xylene is lower than about 4.3, are practically not inflammable. Inside of the inflammable range the flame speed depends on both the level of oxygen and organic matter. In FIG. 1 several curves of flame speed are shown. At the inflammability limits and outside of them the flame speed drops to zero. Generally, the lower the flame speed the safer is the process. The flame speed depends also on the temperature and the diameters of apparatus or tubes. In narrow tubes or in a packing of catalyst even highly explosive gas mixtures may not be ignited. If instead of o-xylene the gas contains naphthalene or phthalic arthydride, then the inflammabilty limits in the appended figure would shift to somewhat lower or higher levels of organic matter, but the shape of the curves would remain very similar. Therefore, for the purpose of illustration, the appended figure is used here also for mixtures which contain either o-xylene and/or phthalic and maleic anhydrides. The ranges indicated by ellipses relate to the following locations:

R1E Reactor 1- Entrance (o-xylene)
R1A Reactor 1- Outlet (Mainly phthalic anhydride)
R2E Reactor 2- Entrance (o-xylene and phthalic anhydride)
R2A Reactor 2- Outlet (Mainly phthalic anhydride)

The process can be operated completely outside of the explosion limits by recycling for example 35% of the waste gas and operating with only 1.0 mol % o-xylene at the inlet of the first reactor. It is also possible to run the process in the range of low flame speed relatively safely thus reducing further the overall gas flow, equipment cost and compression power. The figure provides an illustration of the preferred compositions of the process operating with two reactors.

It is also possible to use three reactors in series. In one example of such embodiment the first uncooled fluid bed reactor is operated at a low concentration of feedstock in the gas and the reactor is used rather to preheat the feed gas. In another embodiment the third reactor serves mainly to complete the conversion. In this reactor a more active catalyst with smaller pellets or with an increased thickness of catalyst is used. In general the use of a third reactor in series does not bring very significant advantages. Two reactors in parallel are considered here as one reactor, because the conditions in both are essentially the same, while two reactors in series can be built into one unit, but this unit is considered as two reactors, because they follow each other and the conditions in each one of them are different.

Thus the invention is a process for the production of phthalic anhydride by catalytic oxidation in the gas phase of the feedstock naphthalene or preferably o-xylene in which at least two reactors in series are applied in such a way that feedstock is added to the reactor effluent gas of one reactor and the gas is then introduced into the next reactor. At the inlet of the last reactor the ratio of moles free oxygen to the moles of organic compounds is lower than 7 and preferably lower than 5. This molar ratio means, that at the inlet of the last reactor the composition of the gas is either in the range of low flame speed or completely outside of the inflammability limits.

In the preferred embodiment only two reactors are used and the gas composition at the inlet of the first reactor is controlled in the range of the lower inflammability limit, while the gas composition at the inlet of the second reactor is controlled closer to the range of the upper limit of inflammability. Both reactors and more specifically the second reactor are preferably tubular reactors cooled by molten salt circulation. At the addition of feedstock to the reaction gas of the first reactor, the temperature drops by 40°–60° C. The feed can be added in form of liquid or as a gas which contains feed. The gas at the inlet of the second reactor contains preferably 10–14 mol % oxygen and about 3 mol % organic compounds (Feedstock, phthalic anhydride, byproducts and intermediate products) and it is essentially non-inflammable. The ratio of moles free oxygen/moles organic compounds in this gas is generally in the range of 4 to 5. In the second reactor more product and more heat is produced and an essentially complete conversion is required. The tubes of the second reactor are therefore substantially longer than the tubes of the first reactor. The reactor is vertical and the gas flows downwards. In the upper part of the second reactor where the partial pressures of oxygen and feedstock are higher, the reaction is faster and a more intensive cooling is desirable to avoid high peak temperatures. In the lower part of the reactor tubes less oxygen and little unconverted feed remains and a more active catalyst of, higher thickness of active layer or smaller pellets is advantageous. Further, in the lower part of the reactor less heat is produced, the gas temperature is dropping, and less intensive cooling is needed. Therefore it is advantageous to flow the molten salt in the same direction as the gas i.e. essentially downwards. In another more preferred embodiment the molten salt is introduced at the middle section of the reactors, flows partly upwards and partly downwards i.e. partly in countercurrent and partly cocurrent flow to the direction of the gas flow. The molten salt is then taken out partly at the upper end and partly at the lower end of the reactor. The molten salt streams taken out at both ends of the reactor are then blended and circulated to the steam generator by an axial pump. Introducing the molten salt at the middle part of the reactor, where the gas temperature is at its peak has several advantages: a lower inlet temperature of molten salt is possible, the peak gas temperature is lower while the outlet gas temperature is slightly higher, the reaction can be completed better and the mass flow off the molten salt is reduced. This method of cooling can be applied with advantage also in processes using only one reactor.

The reaction gas of the second reactor contains typically 3–5 mol % oxygen and 2.4–3 mol % phthalic anhydride and around 0.16 mol % maleic anhydride. At the cooling of this reaction gas for example to 145° C., about one half of the crude product is obtained directly as a liquid. The separation of the rest of the crude product is then done by desublimators periodically switched to melting, by washing the gas with o-xylene or with maleic anhydride or by other well-known methods.

BRIEF DESCRIPTION OF THE DRAWING

The objects, features and advantages of the present invention are illustrated in more detail in the accompanying drawing in which:

The sole FIGURE is a graphical illustration showing the inflammability limits of reaction mixtures as a function of reactant and oxygen concentration at various locations in the apparatus used to perform the process according to the invention.

EXAMPLE 1

In an existing plant the production of crude phthalic anhydride has to be doubled. Instead of installing a complete additional second train, this is achieved at much lower cost with the process of two reactors in series:

An additional reactor, smaller than the existing old one, including a molten salt cooler-steam generator is installed between the compressor and the old reactor. About 10% of the compressed gas is bypassed and added to the effluent gas of the newly installed reactor and more feedstock is added to the thus cooled reaction gas, which is then passed to the old reactor. Downstream of the old two-stage coolers of the reaction gas, a liquid product separator is installed. The existing gas compressor, gas preheater, switch condensers with their cold/hot oil system, the existing gas scrubbers, incinerator and piping can be used. The gas throughput will drop about 10% and the overall pressure drop will remain essentially the same or increase only little. The energy required to compress and heat the gas and melt the crude product remains essentially unchanged at the doubled production. All the additional high pressure steam is available for export. This description of the necessary changes for the doubling of the production is naturally greatly simplified but it clearly illustrates the advantages of the new process.

EXAMPLE 2

For the production of 8000 kg/h of crude phthalic anhydride, 1500 kgmol/h of fresh air are blended with 500 kgmol/h off gas, and a gas containing 16.5 mol % oxygen is obtained. This gas is compressed, preheated mixed with 2756 kg/h (26 kgmol/h) o-Xylene and introduced into a fluid bed reactor. The effluent gas of this reactor is cooled to 370° C. and mixed with 4240 kg/h (40 kgmol/h) liquid o-Xylene, while the temperature drops to 320° C. At the inlet of the second reactor which is a tubular reactor, the gas contains 11.9 mol % free oxygen and 3.1 mol % organic compounds. Finally, the reaction gas of the second reactor contains 3.8 mol % free oxygen and 2.8 mol % phthalic arthydride. This gas is cooled in two stages to 142° C. and 4000 kg/h crude liquid product is separated from the gas. The remaining 4000 kg/h of crude product are recovered in switch-condensers. The cold gas is scrubbed by a solvent such as water recovering maleic arthydride or maleic acid. About 25% of the scrubbed gas is recycled to the compressor, the rest is mixed with air, heated and sent to the incinerator. These examples illustrate the unusually low gas flow at which the process operates. The economic advantages are so significant, that they largely outweigh the slightly more complex controls. The gas flow through the compressor, reactors, switch condensers, etc, is reduced by at least 50% relative to the conventional processes. The compressor power and costs of the plant are very much reduced. Because of the addition of the second reactor, the production of crude phthalic anhydride of an existing plant can be doubled without changing the compressor power or energy requirements.

I claim:

1. A process for making phthalic anhydride by catalytic gas phase oxidation of a reactant selected from the group consisting of o-xylene and naphthalene, said process comprising the steps of:

a) feeding a gas containing oxygen and said reactant to a first reactor;

b) operating said first reactor to oxidize said reactant and obtain an effluent gas including organic compounds selected from the group consisting of said reactant, phthalic anhydride and maleic anhydride;

c) adding said reactant or a gas comprising said reactant to said effluent so that a molar ratio of moles of free oxygen to a sum of moles of said organic compounds in said effluent is less than 7;

d) after the adding of step c), feeding said effluent into a fixed bed reactor following the first reactor; and e) operating said fixed bed reactor to at least partially convert said reactant in said effluent to phthalic anhydride.

2. The process as defined in claim 1, wherein said molar ratio is from 3 to 6 and only two reactors consisting of said first reactor and said fixed bed reactor are used.

3. The process as defined in claim 2, further comprising cooling the gas in the first reactor below 390° C.

4. The process as defined in claim 3, wherein the cooling occurs by passing the gas through a heat exchanger.

5. The process as defined in claim 3, wherein the cooling occurs by addition of a cooling gas to the gas in the first reactor.

6. The process as defined in claim 2, further comprising separating said phthalic anhydride from an effluent from the fixed bed reactor to form a waste gas, blending from 15 to 35% of said waste gas with air to form a gas mixture, compressing the gas mixture and recycling the gas mixture to the first reactor.

7. The process as defined in claim 2, wherein less than 97% conversion of said reactant to said phthalic anhydride occurs in said first reactor.

8. The process as defined in claim 2, wherein said first reactor is a fluid bed reactor.

9. The process as defined in claim 2, wherein said first reactor is a tubular reactor cooled by molten salt flowing in a countercurrent direction to a flow of the gas therein.

10. The process as defined in claim 2, wherein the fixed bed reactor is a tubular reactor in a last portion of which molten salt flows in a flow direction with said gas therein.

11. The process as defined in claim 10, wherein said molten salt is heated up by at least 30° C. in the second reactor.

12. The process as defined in claim 2, wherein said first reactor is a tubular reactor cooled by molten salt flowing in a countercurrent direction to a flow of the gas therein and the fixed bed reactor is another tubular reactor in a last portion of which said molten salt flows in a gas flow direction therein with said gas and is thereby heated up at least 30° C. in the second reactor.

13. The process as defined in claim 2, wherein the fixed bed reactor is a tubular reactor having a lower part containing a catalyst having a comparatively higher activity and an upper part containing a catalyst having a comparatively lower activity.

14. The process as defined in claim 2, wherein the fixed bed reactor is a tubular reactor having a lower part containing a catalyst having a comparatively smaller pellets and an upper part containing a catalyst having a comparatively larger pellets.

15. The process as defined in claim 2, wherein the fixed bed reactor is a tubular reactor having a lower part containing a comparatively thicker catalyst layer and an upper part containing a comparatively thinner catalyst layer.

16. The process as defined in claim 2, wherein said reactant is said o-xylene and said gas fed to said first reactor contains from 1 to 1.4 mole-% of said o-xylene.

17. The process as defined in claim 2, wherein said reactant is said o-xylene and said gas fed to said first reactor contains less than from 1.1 mole-% of said o-xylene.

18. The process as defined in claim 2, wherein said reactant is said o-xylene and said gas fed to said first reactor contains less than 1.8 mole-% of said o-xylene.

* * * * *